May 23, 1972 W. T. STRAW Plant Pat. 3,193

ORNAMENTAL PEAR TREE

Filed Oct. 5, 1970

WILLIAM T. STRAW
INVENTOR

BY Spensley, Horn & Lubitz
ATTORNEYS

United States Patent Office

Plant Pat. 3,193
Patented May 23, 1972

3,193

ORNAMENTAL PEAR TREE

William T. Straw, 47 McCullum Road,
Independence, Ky. 41051

Filed Oct. 5, 1970, Ser. No. 78,312
Int. Cl. A01h 5/03
U.S. Cl. Plt.—36 1 Claim

ABSTRACT OF THE DISCLOSURE

An ornamental pear tree of the Pyrus calleryana variety is disclosed. The thornless tree is characterized by leaves which are three to four inches in length, two to three inches wide and ovate in shape. The branches of the tree are substantially horizontal from the trunk with slight upward sweeps near their tips. The annual growth color of new branches is brown with a touch of red. The leaves of the tree during the summer are medium to dark green with a very glossy top surface.

BACKGROUND OF THE INVENTION (1) The invention relates to the field of ornamental pear trees.

(2) Prior ornamental pear trees.

The closest known ornamental pear tree to the presently disclosed tree is the so-called Bradford Ornamental Pear Tree. A somewhat detailed description of this tree may be found in the U.S. Department of Agriculture, Home and Garden Bulletin No. 154 issued October 1968. As will be pointed out herein the presently disclosed ornamental pear tree has several distinctions over the Bradford including a more horizontal limb or branch formation, glossier and darker green leaves with a wavier edge and a brown to reddish branch color on newly grown branches. Additionally, the leaves have an ovate shape in the presently described tree as compared to an oval shape in the Bradford. Petioles of the Bradford are 1¼ to 2 inches long whereas on the discovered tree they are 2 to 3 inches long and green with a red blush.

DETAILED DESCRIPTION OF THE INVENTION

Figure 1:
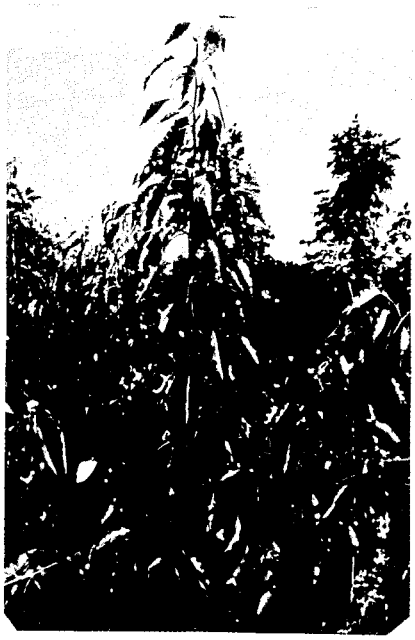
FIG. 1 is a view of substantially an entire tree of the newly disclosed variety, the tree being approximately 12 feet tall.
Figure 2:
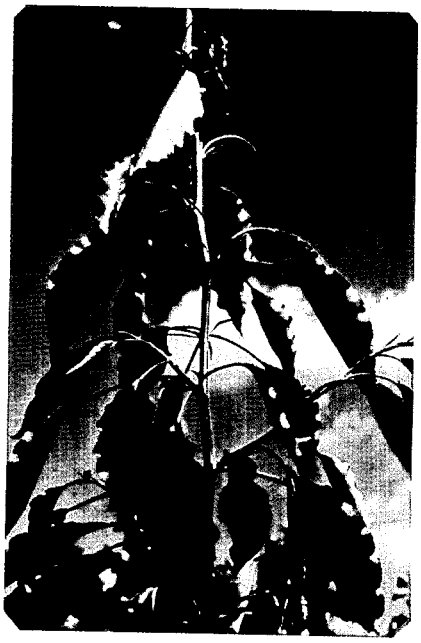
FIG. 2 is a close-up view of the upper portion of the newly disclosed tree illustrating the trunk, several branches, and several leaves; and, FIG. 3 is a close-up view of the leaves of the newly disclosed ornamental pear tree.
Figure 3:
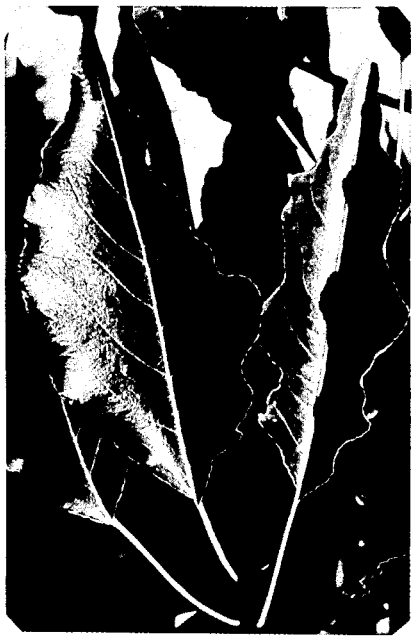

The original tree was discovered in the applicant's nursery located in Independence, Ky., during February 1969. It appeared as a tree having different characteristics than the other approximately 100 seedlings of *Pyrus calleryana* included in a planting made in April 1966. All the remaining pear trees of this planting developed into thorny trees except the one disclosed herein, which is thornless. During the spring of 1969, the presently disclosed tree was grafted and budded with the thorny *Pyrus calleryanas*. The original seedling and the grafted and budded trees were observed during the 1969 and 1970 growing season.

The characteristic of the original seedling and of the asexually reproduced trees are as follows (referring to the figures):

(1) Form.—The original tree is now approximately six years old, twelve feet tall and approximately ten feet wide with a trunk diameter of approximately three inches. The tree is a pyramidal in shape with the branches attached at approximately right angles to the trunk. The branches having a slightly upward sweep near their tips. The tree thus has a strong horizontal limb formation. The grafted and budded trees are similar in form and grew five to six feet in height and four to five feet in width during 1969.

(2) Thorns.—Unlike the normal *Pyrus calleryana* which is very thorny the presently disclosed tree is thorn-free.

(3) Foliage.—The leaves are ovate in shape, pointed and three to five inches in length and two to three inches wide with a wavy margin. The summer color is medium to dark green and the leaves have a very glossy top surface. The petioles are light green with a red blush. The fall foliage color is red-purple to purple with a valve of 2.9 to 3.0, an intensity of five to six and as high as 7.5 (Munsell Color Chart). The peak of the fall color on these trees was reached after most other trees were dormant and defoliated.

(4) Bark color.—Trunk bark color is medium gray. Annual growth color of new branching is brown with a touch of red. On the newest growths the red is more pronounced.

(5) Growth habits.—The growth pattern of the disclosed pear tree is extremely vigorous. In 1969 grafts on established *Pyrus calleryana* understalks grew up to five and six feet in height and four to five feet in width.

(6) Flowers.—The six year old tree has had five bloom clusters, four to five inches in width and near white in color. Two clusters matured very small pears of russet texture, of about ¼ to ½ in diameter.

(7) Disease and insect resistance.—Although unsprayed in 1969, growth was vigorous and clean of disease and showed only very light insect damage.

Comparison of the invented tree with the normal seedlings of *Pyrus calleryana*.—The normal seedlings of the *Pyrus calleryana* have leaves approximately ¼ as large as the presently disclosed tree and the foliage is thinner with a considerable color variation in autumn among the various *Pyrus calleryana* seedlings. The presently disclosed tree has larger foliage of a heavier texture and wavy edges on the leaves with the upper surfaces of the leaves having a glossy surface. Additionally, the presently disclosed tree has a more brilliant fall color. Unlike the normal seedlings of *Pyrus calleryana* the presently disclosed tree is thorn-free.

Comparison of the disclosed tree to the Bradford.—The presently disclosed tree is broadly pyramidal in shape and has a tendency towards horizontal branching, as compared with the Bradford's more slender form of upright branching. The foliage of the presently disclosed tree is thicker, a more dark green, glossier and the waves on the leaf edges are more pronounced. Leaves in the presently disclosed tree are oviate, more pointed and are one to one and-a-half inches longer than those on the Bradford.

The petioles are green with a red blush as compared to the green of the Bradford. The fall foliage color is more consistently red or red-purple on the disclosed tree than the coloring on the Bradford trees.

I claim:

1. The new and distinct variety of ornamental pear tree substantially as herein shown and described and characterized by its broadly pyramidal shape, horizontal branching and thick foliage.

No references cited.

ROBERT E. BAGWILL, Primary Examiner